US012678144B2

(12) United States Patent
Kruecker et al.

(10) Patent No.: US 12,678,144 B2

(45) Date of Patent: *Jul. 14, 2026

---

(54) SYSTEM AND METHOD FOR REAL-TIME FUSION OF ACOUSTIC IMAGE WITH REFERENCE IMAGE

(71) Applicant: KONINKLIJKE PHILIPS N.V., Eindhoven (NL)

(72) Inventors: Jochen Kruecker, Andover, MA (US); Grzegorz Andrzej Toporek, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 19/042,949

(22) Filed: Jan. 31, 2025

(65) Prior Publication Data

US 2025/0176946 A1 Jun. 5, 2025

Related U.S. Application Data

(63) Continuation of application No. 17/630,262, filed as application No. PCT/EP2020/070895 on Jul. 24, 2020, now Pat. No. 12,239,491.

(Continued)

(51) Int. Cl.
*A61B 8/00* (2006.01)
*A61B 8/14* (2006.01)
(Continued)

(52) U.S. Cl.
CPC .............. *A61B 8/5261* (2013.01); *A61B 8/14* (2013.01); *A61B 8/4254* (2013.01);
(Continued)

(58) Field of Classification Search
CPC . A61B 6/5247; A61B 8/5261; G06T 2200/04; G06T 2207/10081;
(Continued)

(56) References Cited

U.S. PATENT DOCUMENTS

| | | | |
|---|---|---|---|
| 9,710,910 B2 | 7/2017 | Kim et al. | |
| 9,968,257 B1 | 5/2018 | Burt | |

(Continued)

FOREIGN PATENT DOCUMENTS

| | | |
|---|---|---|
| CN | 107798697 A | 3/2018 |
| WO | 2019048482 A1 | 3/2019 |

OTHER PUBLICATIONS

Chen et al. "Registration of CT and Ultrasound Images of the Spine with Neural Network and Orientation Code Mutual Information." Medical Imaging and Augmented Reality. MIAR 2016. Lecture Notes in Computer Science( ), vol. 9805 (Year: 2016).*

(Continued)

*Primary Examiner* — Amelie R Davis

(57) ABSTRACT

A system and method for registering two dimensional (2D) acoustic images to a three dimensional (3D) reference image. The method comprises steps to access a 3D reference image of a region of interest (ROI) in a subject, segment the ROI to define a reference 3D coordinate system, acquire 2D acoustic images of the ROI without absolute spatial tracking, generate a standardized predicted pose for the 2D acoustic images with respect to a standardized 3D coordinate system which was defined for a plurality of previously-obtained 3D images of corresponding ROIs other subjects which were obtained using the 3D imaging modality, convert the standardized predicted poses for the 2D acoustic images from the standardized 3D coordinate system to reference predicted poses in the reference 3D coordinate system, and use the reference predicted poses for the 2D (Continued)

710
722C
722
722D
722A
722B acoustic images to register the 2D acoustic images to the 3D reference image.

16 Claims, 10 Drawing Sheets

Related U.S. Application Data

(60) Provisional application No. 62/881,002, filed on Jul. 31, 2019.

(51) Int. Cl.
| | |
|---|---|
| *G06T 7/11* | (2017.01) |
| *G06T 7/30* | (2017.01) |
| *G06T 7/70* | (2017.01) |

(52) U.S. Cl.
CPC ............ *A61B 8/4488* (2013.01); *A61B 8/463* (2013.01); *A61B 8/466* (2013.01); *G06T 7/11* (2017.01); *G06T 7/30* (2017.01); *G06T 7/70* (2017.01); *G06T 2200/04* (2013.01); *G06T 2207/10081* (2013.01); *G06T 2207/10088* (2013.01); *G06T 2207/10132* (2013.01); *G06T 2207/20084* (2013.01); *G06T 2207/20221* (2013.01); *G06T 2207/30004* (2013.01)

(58) Field of Classification Search
CPC . G06T 2207/10088; G06T 2207/10132; G06T 2207/20084; G06T 2207/20221; G06T 2207/30004; G06T 7/11; G06T 7/30; G06T 7/70
See application file for complete search history.

(56) References Cited

U.S. PATENT DOCUMENTS

| | | |
|---|---|---|
| 2016/0317119 A1 | 11/2016 | Maraghoosh et al. |
| 2018/0330497 A1 | 11/2018 | Kapoor et al. |

OTHER PUBLICATIONS

International Search Report and Written Opinion for PCT/EP2020/070895, Mailing date: Feb. 11, 2020, 15 pages.

Huang, Qing-Hua et al., "Volume Reconstruction of Freehand three-dimensional Ultrasound using Median Filters", Ultrasonics, 2008, vol. 48, Issue 3, pp. 182-192.

Xue, E.Y., "Sensorless Ultrasound Probe 6DoF Pose Estimation Through the Use of CNNs on Image Data", Retrieved from https://dspace.mit.edu/handle/1721.1/119697; 2018, 57 Pages.

Silva, T. et al., "Real-time, image-based slice-to-volume registration for ultrasound-guided spinal intervention", Phys Med Biol., 2018, 63(21), 215016, 13 Pages.

Penney, G.P. et al., "Registration of freehand 3D ultrasound and magneticresonance liver images", Medical Image Analysis, 2004, 8, pp. 81-91.

Hu, Y. et al., Weakly-supervised convolutional neural networks for multimodalimage registration, Medical Image Analysis, 2018, 49, pp. 1-13.

* cited by examiner

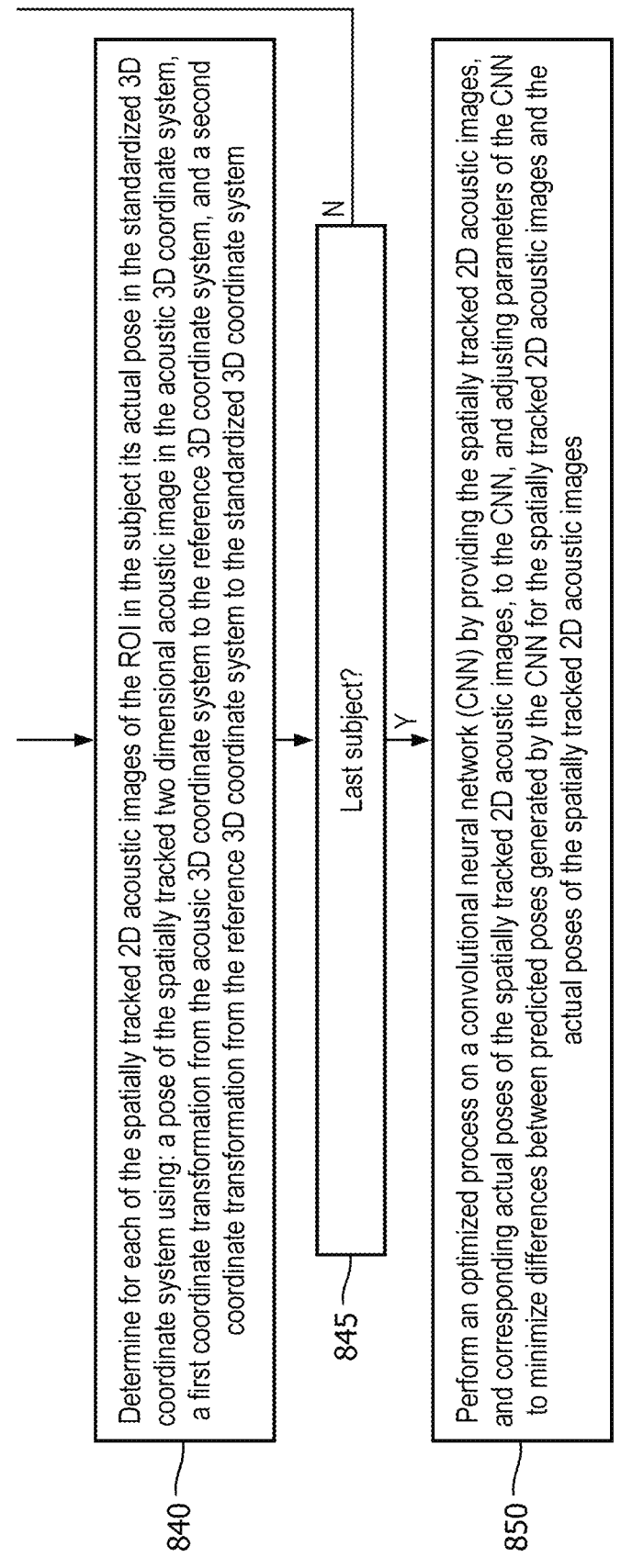

840 — Determine for each of the spatially tracked 2D acoustic images of the ROI in the subject its actual pose in the standardized 3D coordinate system using: a pose of the spatially tracked two dimensional acoustic image in the acoustic 3D coordinate system, a first coordinate transformation from the acousic 3D coordinate system to the reference 3D coordinate system, and a second coordinate transformation from the reference 3D coordinate system to the standardized 3D coordinate system 845 — Last subject?

N

Y

850 — Perform an optimized process on a convolutional neural network (CNN) by providing the spatially tracked 2D acoustic images, and corresponding actual poses of the spatially tracked 2D acoustic images, to the CNN, and adjusting parameters of the CNN to minimize differences between predicted poses generated by the CNN for the spatially tracked 2D acoustic images and the actual poses of the spatially tracked 2D acoustic images

FIG. 8 continued

SYSTEM AND METHOD FOR REAL-TIME FUSION OF ACOUSTIC IMAGE WITH REFERENCE IMAGE

CROSS-REFERENCE TO PRIOR APPLICATIONS

This application is a continuation application of co-pending U.S. patent application Ser. No. 17/630,262 entitled "System and Method for Real-Time Fusion of Acoustic Image with Reference Image", filed on Jan. 26, 2022, which in turn is a the U.S. National Phase application under 35 U.S.C. § 371 of International Application No. PCT/EP2020/070895, filed on Jul. 24, 2020, which claims the benefit of U.S. Provisional Patent Application No. 62/881,002, filed on Jul. 31, 2019. These applications are hereby incorporated by reference herein.

TECHNICAL FIELD

This invention pertains to acoustic (e.g., ultrasound) imaging, and in particular a system, device and method for real-time fusion of an acoustic image with a reference image.

BACKGROUND AND SUMMARY

Acoustic (e.g., ultrasound) imaging systems are increasingly being employed in a variety of applications and contexts.

Acoustic imaging is inherently based on hand-held acoustic probe motion and positioning, thus lacking the absolute three dimensional (3D) reference frame and anatomical context of other modalities such as computed tomography (CT) and magnetic resonance imaging (MRI). This makes interpreting the acoustic images (which are typically two dimensional (2D)), or relating them to corresponding anatomy in images obtained with other modalities, challenging. In addition, it is often desirable to have 3D views of structures, but 3D acoustic is relatively expensive and less commonly used.

In order to obtain 3D volumetric images from hand-held 2D acoustic probes, spatial tracking of the probe is required in order to "reconstruct" a 3D volume image from a sequence of individual, spatially localized, 2D images. Furthermore, it is often desirable to co-register and/or fuse 2D or 3D acoustic images with other modalities such as CT or MRI.

Until now, this has required additional hardware, such as optical or electromagnetic tracking systems, and involved additional work steps and time to set up and calibrate the system, adding expense and time to the imaging procedure. In order to obtain a registration between acoustic and another imaging modality, for example, it is required to identify common fiducials, common anatomical landmarks, or perform a registration based on image contents, all of which can be challenging, time consuming, and prone to error. A tracking system also typically puts constraints on how the acoustic probe can be used, e.g. by limiting the range of motion. Fully "internal" tracking systems, e.g. based on inertial sensors, exist but are limited in accuracy, suffer from long-term drift, and do not provide an absolute coordinate reference needed to relate or register the acoustic image information to image data obtained via other modalities.

These barriers have significantly impeded the adoption of "fusion ultrasound" imaging, despite obvious clinical benefits such as increased diagnostic confidence, better guidance of interventional procedures, or better ability to document findings.

Accordingly, it would be desirable to provide a system and a method which can address these challenges. In particular, it would be desirable to provide a system and method which can register and fuse acoustic images obtained in the absence of any tracking devices with images obtained via other imaging modalities such as MRI.

In one aspect of the invention, a system comprises an acoustic probe and an acoustic imaging instrument connected to the acoustic probe. The acoustic probe has an array of acoustic transducer elements, and is not associated with any tracking device. The acoustic probe is configured to transmit one or more acoustic signals to a region of interest (ROI) in a subject and is further configured to receive acoustic echoes from the region of interest. The acoustic imaging instrument comprises a communication interface and a processing system. The communication interface is configured to provide transmit signals to at least some of the acoustic transducer elements. The transmit signals cause the array of acoustic transducer elements to transmit the one or more acoustic signals to the ROI in the subject. The communication interface is configured to receive one or more image signals from the acoustic probe. The image signals are produced from the acoustic echoes from the region of interest. The processing system is configured to: access a three dimensional reference image of the ROI in the subject, wherein the three dimensional reference image is obtained using a first imaging modality. The processing system is configured to segment the ROI in the three dimensional reference image. The processing system is configured to employ the segmented ROI in the three dimensional reference image to define a reference three dimensional coordinate system for the three dimensional reference image. The processing system is configured to acquire a plurality of two dimensional acoustic images of the ROI in the subject from the image signals. The processing system is configured to generate a standardized predicted pose for each of the plurality of two dimensional acoustic images of the ROI with respect to a standardized three dimensional coordinate system, wherein the standardized three dimensional coordinate system was defined for a plurality of previously-obtained three dimensional images of corresponding ROIs in a plurality of other subjects. The processing system is configured to convert the standardized predicted pose for each of two dimensional acoustic images of the ROI in the subject from the standardized three dimensional coordinate system to a reference predicted pose in the reference three dimensional coordinate system. The processing system is configured to use the standardized predicted pose to register each of the two dimensional acoustic images to the three dimensional reference image.

In some embodiments, the system further comprises a display device, wherein the system is configured to display on the display device at least one of the two dimensional acoustic images together with a corresponding two dimensional slice of the three dimensional reference image.

In some embodiments, the system further comprises a display device, and is configured to use the standardized predicted poses to display on the display device a plurality of two dimensional acoustic images in the standardized three dimensional coordinate system.

In some embodiments, the processing system is further configured to construct a three dimensional acoustic image for the ROI in the subject from the two dimensional acoustic images and their corresponding predicted poses.

In some embodiments, the system further comprises a display device, wherein the system is configured to display on the display device the reference three dimensional image and the three dimensional acoustic image in a common three dimensional coordinate system.

In some embodiments, the ROI in the subject includes an organ, and segmenting the ROI in the three dimensional reference image comprises segmenting the organ.

In some embodiments, generating the standardized predicted pose for each of the two dimensional acoustic images of the ROI in the subject with respect to the standardized three dimensional coordinate system comprises applying each of the two dimensional acoustic images to a convolutional neural network, wherein the convolutional neural network been trained to predict standardized predicted poses of two dimensional acoustic images in the standardized three dimensional coordinate system by using the previously-obtained three dimensional images of the corresponding ROIs in the plurality of other subjects, wherein the previously-obtained three dimensional images of the corresponding ROIs in the plurality of other subjects were obtained using the first imaging modality.

In some embodiments, the two dimensional acoustic images comprises a series of two dimensional images, and generating the standardized predicted pose for each of the two dimensional acoustic images of the ROI in the subject with respect to the standardized three dimensional coordinate system comprises generating standardized predicted poses for the series of two dimensional images by averaging the standardized predicted poses over all of the two dimensional acoustic images of the series.

In another aspect of the invention, a method comprises: accessing a three dimensional reference image of a region of interest (ROI) in a subject, wherein the three dimensional reference image was obtained using a first imaging modality; segmenting the ROI in the three dimensional reference image; employing the segmented ROI in the three dimensional reference image to define a reference three dimensional coordinate system for the three dimensional reference image; employing an acoustic probe to acquire a plurality of two dimensional acoustic images of the ROI in the subject without spatial tracking of the acoustic probe; generating a standardized predicted pose for each of the plurality of two dimensional acoustic images of the ROI in the subject with respect to a standardized three dimensional coordinate system, wherein the standardized three dimensional coordinate system was defined for a plurality of previously-obtained three dimensional images of corresponding ROIs in a plurality of other subjects, wherein the plurality of previously-obtained three dimensional images of corresponding ROIs in a plurality of other subjects were obtained using the first imaging modality; converting the standardized predicted pose for each of the two dimensional acoustic images of the ROI in the subject from the standardized three dimensional coordinate system to a reference predicted pose in the reference three dimensional coordinate system; and using the reference predicted pose to register each of the two dimensional acoustic images to the three dimensional reference image.

In some embodiments, the method further comprises displaying on a display device at least one of the two dimensional acoustic images together with a corresponding two dimensional slice of the three dimensional reference image.

In some embodiments, the method further comprises using the standardized predicted poses to display on a display device a plurality of two dimensional acoustic images in the standardized three dimensional coordinate system.

In some embodiments, the method further comprises constructing a three dimensional acoustic image for the ROI in the subject from the two dimensional acoustic images and their corresponding predicted poses.

In some embodiments, the method further comprises displaying on a display device the reference three dimensional image and the three dimensional acoustic image in a common three dimensional coordinate system.

In some embodiments, the ROI in the subject includes an organ, and wherein segmenting the ROI in the three dimensional reference image comprises segmenting the organ.

In some embodiments, generating the standardized predicted pose for each of one or more two dimensional acoustic images of the ROI in the subject with respect to the standardized three dimensional coordinate system comprises applying each of the one or more two dimensional acoustic images to a convolutional neural network, wherein the convolutional neural network has been trained to generate standardized predicted poses of two dimensional acoustic images in the standardized three dimensional coordinate system by using the previously-obtained three dimensional images of the corresponding ROIs in the plurality of other subjects, wherein the previously-obtained three dimensional images of the corresponding ROIs in the plurality of other subjects were obtained using the first imaging modality.

In some embodiments, the two dimensional acoustic images comprises a series of two dimensional images, and wherein generating the standardized predicted pose for each of the two dimensional acoustic images of the ROI in the subject with respect to the standardized three dimensional coordinate system comprises generating standardized predicted poses for the series of two dimensional images by averaging the standardized predicted poses over all of the two dimensional acoustic images of the series.

In another aspect of the invention, a method includes defining a standardized three dimensional coordinate system for a plurality of three dimensional reference images of corresponding ROIs in a plurality of subjects, wherein the three dimensional reference images were obtained using a first imaging modality. The method further includes, for each of the plurality of subjects: obtaining a series of spatially tracked two dimensional acoustic images of the ROI in the subject; constructing a three dimensional acoustic image of the ROI in the subject from the series of spatially tracked two dimensional acoustic images of the ROI, wherein the three dimensional acoustic image of the ROI in the subject is in an acoustic three dimensional coordinate system; accessing a selected three dimensional reference image among the plurality of three dimensional reference images, wherein the selected three dimensional reference image is of the ROI in the subject; segmenting the three dimensional reference image of the ROI in the subject; defining a reference three dimensional coordinate system for the reference image of the ROI in the subject, based on the segmentation; determining for each of the spatially tracked two dimensional acoustic images of the ROI in the subject its actual pose in the standardized three dimensional coordinate system using: a pose of the spatially tracked two dimensional acoustic image in the acoustic three dimensional coordinate system, a first coordinate transformation from the acoustic three dimensional coordinate system to the reference three dimensional coordinate system, and a second coordinate transformation from the reference three dimensional coordinate system to the standardized three dimensional coordinate system; and performing an optimization process on a convolutional neural network (CNN) by providing the spatially tracked two dimensional acoustic images, and the corresponding actual poses of the spatially tracked two dimensional acoustic images, to the CNN and adjusting parameters of the CNN to minimize differences between predicted poses generated by the CNN for the spatially tracked two dimensional acoustic images and the actual poses of the spatially tracked 2D acoustic images. The optimization may be performed using batches of the spatially tracked two dimensional acoustic images, and may include in some or all of the batches spatially tracked two dimensional acoustic images from different subjects.

In some embodiments, the ROI in the subject includes a reference structure, such as an organ, a known vein, or a joint, and wherein segmenting the three dimensional reference image of the ROI in the subject comprises segmenting the organ.

In some embodiments, the first imaging modality is magnetic resonance imaging.

In some embodiments, obtaining the series of spatially tracked two dimensional acoustic images of the ROI in the subject comprises receiving one or more imaging signals from an acoustic probe in conjunction with receiving a signal which spatially tracks a location of the acoustic probe while it provides the one or more imaging signals.

DETAILED DESCRIPTION

As discussed above, it is often desirable to co-register and/or fuse two dimensional (2D) and/or three dimensional (3D) acoustic images obtained with other imaging modalities such as CT or MRI.

Until now, this has required additional hardware, such as optical or electromagnetic tracking devices or systems, and involved additional work steps and time to set up and calibrate the system, adding expense and time to the imaging procedure.

Figure 1:
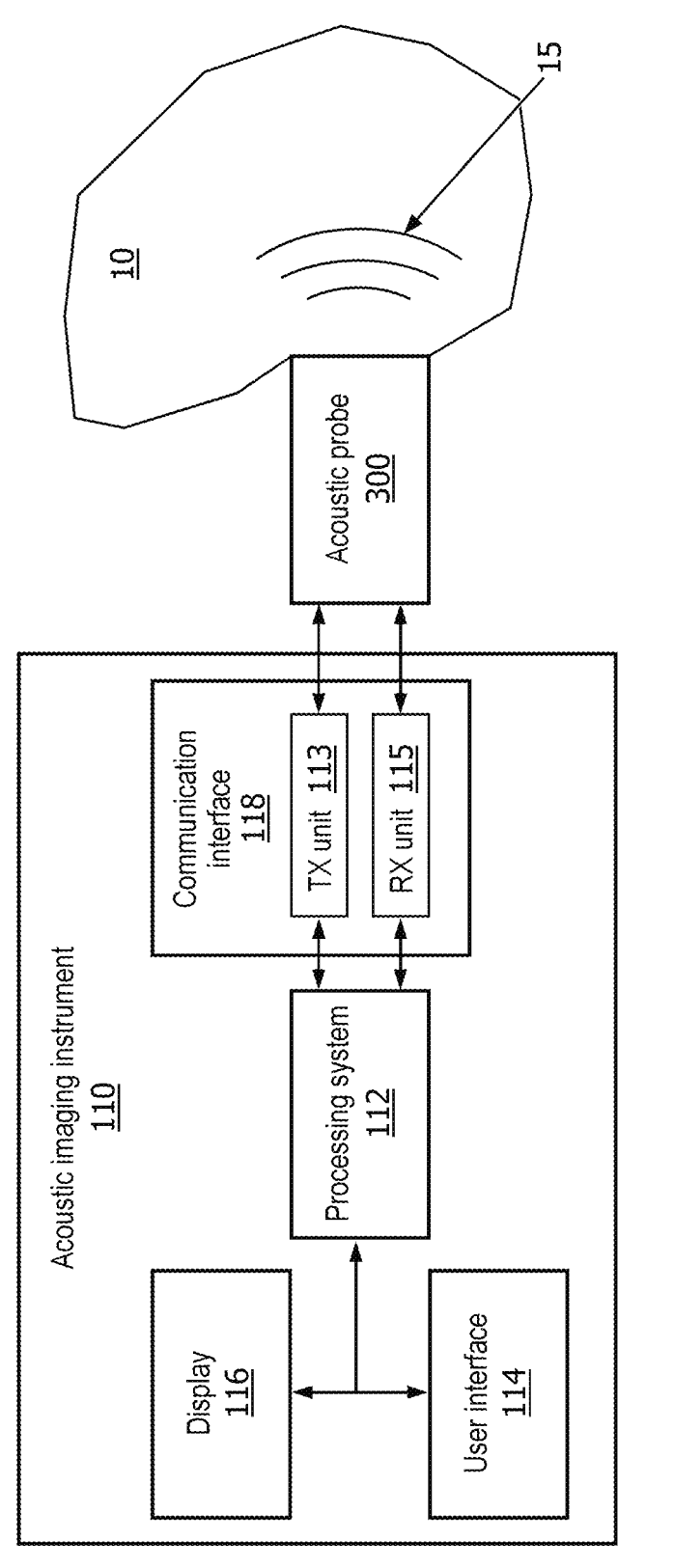
FIG. 1 illustrates an example embodiment of an acoustic imaging system.

FIG. 1 illustrates an example embodiment of an acoustic imaging system 100 which includes an acoustic imaging instrument 110 and an acoustic probe 300. Acoustic imaging instrument 110 includes a processing system 112, a user interface 114, a display device 116 and a communication interface 118 and which may be employed in a method of fusing acoustic images, obtained in the absence of any tracking devices or systems, with images obtained via other imaging modalities, such as magnetic resonance imaging, MRI, computed tomography (CT), cone beam computed tomography (CBCT), etc.

It should be understood that in various embodiments, acoustic imaging system 100 may be configured differently than described below with respect to FIG. 1. In particular, in different embodiments, one or more functions described as being performed by elements of acoustic imaging instrument 110 may instead be performed in acoustic probe 300 depending, for example, on the level of signal processing capabilities which might be present in acoustic probe 300.

In various embodiments, processing system 112 may include various combinations of processing system 20 shown in FIG. 2, which will be described below in greater detail One or more memories depicted in processing system 20 (e.g., nonvolatile memory Flash memory 234), included within processing system 112, may store therein computer-readable instructions which cause a processing element of processing system 112 to execute an algorithm to control acoustic imaging system 100 to perform one or more operations or methods which are described in greater detail below. In some embodiments, processing system 112 may execute an operating system. In some embodiments, processing system 112 may execute instructions which present a user of acoustic imaging system 100 with a graphical user interface (GUI) via user interface 114 and display device 116.

In various embodiments, user interface 114 may include any combination of a keyboard, keypad, mouse, trackball, stylus/touch pen, joystick, microphone, speaker, touchscreen, one or more switches, one or more knobs, one or more buttons, one or more lights, etc. In some embodiments, a microprocessor of processing system 112 may execute a software algorithm which provides voice recognition of a user's commands via a microphone of user interface 114.

Display device 116 may comprise a display screen of any convenient technology (e.g., liquid crystal display). In some embodiments the display screen may be a touchscreen device, also forming part of user interface 114.

Communication interface 118 includes a transmit unit 113 and a receive unit 115.

Transmit unit 113 may generate one or more electrical transmit signals under control of processing system 112 and supply the electrical transmit signals to acoustic probe 300. Transmit unit 113 may include various circuits as are known in the art, such as a clock generator circuit, a delay circuit and a pulse generator circuit, for example. The clock generator circuit may be a circuit for generating a clock signal for setting the transmission timing and the transmission frequency of a drive signal. The delay circuit may be a circuit for setting delay times in transmission timings of drive signals for individual paths corresponding to the transducer elements of acoustic probe 300 and may delay the transmission of the drive signals for the set delay times to concentrate the acoustic beams to produce acoustic probe signal 15 having a desired profile for insonifying a desired acoustic image plane. The pulse generator circuit may be a circuit for generating a pulse signal as a drive signal in a predetermined cycle.

Receive unit 115 is configured to receive the one or more acoustic image signals from acoustic probe 300 and to process the acoustic image signal(s) to produce acoustic image data from which 2D acoustic images may be produced. In some embodiments, receive unit 115 may include various circuits as are known in the art, such as one or more amplifiers, one or more A/D conversion circuits, and a phasing addition circuit, for example. The amplifiers may be circuits for amplifying the acoustic image signals at amplification factors for the individual paths corresponding to the transducer elements 322 (shown in FIG. 3). The A/D conversion circuits may be circuits for performing analog/digital conversion (A/D conversion) on the amplified acoustic image signals. The phasing addition circuit is a circuit for adjusting time phases of the amplified acoustic image signals to which A/D conversion is performed by applying the delay times to the individual paths respectively corresponding to the transducer elements 322 and generating acoustic data by adding the adjusted received signals (phase addition). The acoustic data may be stored in memory associated with acoustic imaging instrument 100.

Processing system 112 may reconstruct acoustic data received from receiver unit 115 into a 2D acoustic image corresponding to an acoustic image plane which intercepts area of interest 10, and subsequently causes display device 116 to display this 2D acoustic image. The reconstructed 2D acoustic image may for example be an ultrasound Brightness-mode "B-mode" image, otherwise known as a "2D mode" image, a "C-mode" image or a Doppler mode image, or indeed any acoustic image.

In various embodiments, processing system 112 may include a processor (e.g., processor 200) which may execute software in one or more modules for performing one or more algorithms or methods as described below with respect to FIGS. 8 and 9.

Of course it is understood that acoustic imaging instrument 110 may include a number of other elements not shown in FIG. 1, for example a power system for receiving power from AC Mains, an input/output port for communications between processor 112 and acoustic probe 300, a communication subsystem for communicating with other eternal devices and systems (e.g., via a wireless, Ethernet and/or Internet connection), etc.

In some embodiments, acoustic imaging instrument 110 also receives an inertial measurement signal from an inertial measurement unit (IMU) included in or associated with acoustic probe 300 as described below with respect to FIG. 3. The inertial measurement signal may indicate an orientation or pose of acoustic probe 300. The inertial measurement unit may include a hardware circuit, a hardware sensor or Microelectromechanical systems (MEMS) device. The inertial measurement circuit may include a processor, such as processing system 200, running software in conjunction with a hardware sensor or MEMS device.

In other embodiments, acoustic imaging instrument 100 does not receive any inertial measurement signal, but may determine a relative orientation or pose of acoustic probe 300 as described in greater detail below, for example with respect to FIG. 9.

Figure 2:
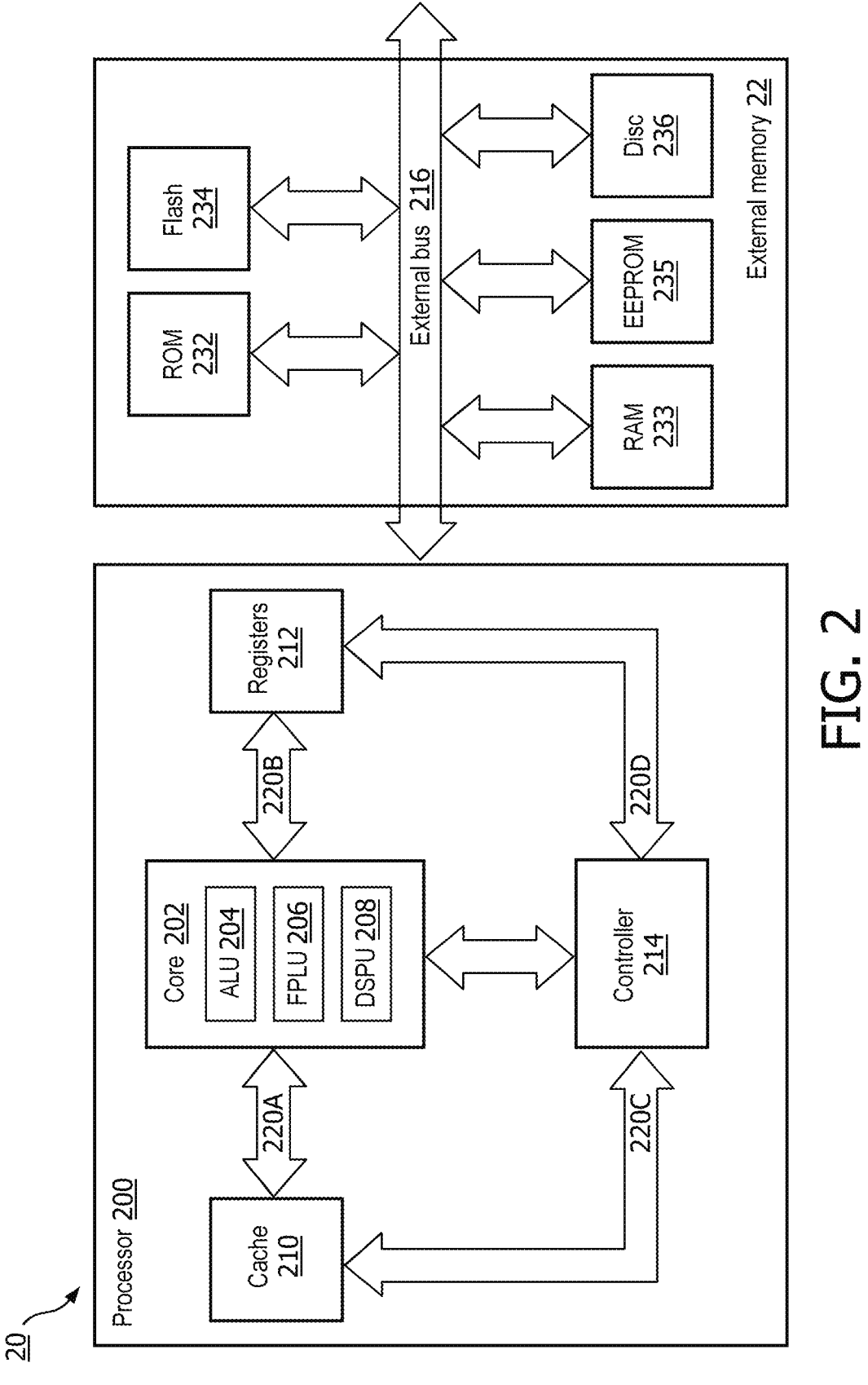
FIG. 2 illustrates an example embodiment of a processing unit which may be included in an acoustic imaging apparatus and/or an apparatus for registering and fusing acoustic images obtained in the absence of any tracking devices with images obtained via other imaging modalities.

FIG. 2 is a block diagram illustrating an example processing system 20 according to embodiments of the disclosure. Processing system 20 may be used to implement one or more processing systems described herein, for example, processing system 112 shown in FIG. 1. FIG. 2 illustrates an example embodiment of a processing system 20 which may be included in an acoustic imaging system (e.g., acoustic imaging system 100) and/or an apparatus (e.g., acoustic imaging instrument 110) for registering and fusing acoustic images of a region of interest (ROI) of a subject obtained in the absence of any tracking devices, with images of the ROI in the subject which were obtained via other imaging modalities such as magnetic resonance imaging (MRI).

Processing system 20 includes a processor 200 connected to external memory 22, including one or more external memory devices, by an external bus 216.

Processor 200 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

Processor 200 may include one or more cores 202. The core 202 may include one or more arithmetic logic units (ALU) 204. In some embodiments, the core 202 may include a floating point logic unit (FPLU) 206 and/or a digital signal processing unit (DSPU) 208 in addition to or instead of the ALU 204.

Processor 200 may include one or more registers 212 communicatively coupled to the core 202. The registers 212 may be implemented using dedicated logic gate circuits (e.g., flip-flops) and/or any memory technology. In some embodiments the registers 212 may be implemented using static memory. The register may provide data, instructions and addresses to the core 202.

In some embodiments, processor 200 may include one or more levels of cache memory 210 communicatively coupled to the core 202. The cache memory 210 may provide computer-readable instructions to the core 202 for execution. The cache memory 210 may provide data for processing by the core 202. In some embodiments, the computer-readable instructions may have been provided to the cache memory 210 by a local memory, for example, local memory attached to the external bus 216. The cache memory 210 may be implemented with any suitable cache memory type, for example, metal-oxide semiconductor (MOS) memory such as static random access memory (SRAM), dynamic random access memory (DRAM), and/or any other suitable memory technology.

Processor 200 may include a controller 214, which may control input to the processor 200 from other processors and/or components included in a system (e.g., user interface 114 shown in FIG. 1) and/or outputs from the processor 200 to other processors and/or components included in the system (e.g., communication interface 118 shown in FIG. 1). Controller 214 may control the data paths in the ALU 204, FPLU 206 and/or DSPU 208. Controller 214 may be implemented as one or more state machines, data paths and/or dedicated control logic. The gates of controller 214 may be implemented as standalone gates, FPGA, ASIC or any other suitable technology.

Registers 212 and the cache 210 may communicate with controller 214 and core 202 via internal connections 220A, 220B, 220C and 220D. Internal connections may implemented as a bus, multiplexor, crossbar switch, and/or any other suitable connection technology.

Inputs and outputs for processor 200 may be provided via external bus 216, which may include one or more conductive lines. External bus 216 may be communicatively coupled to one or more components of processor 200, for example the controller 214, cache 210, and/or register 212.

External bus 216 may be coupled to external memory which includes one or more external memory devices. The external memory devices may include Read Only Memory (ROM) 232. ROM 232 may be a masked ROM, Electronically Programmable Read Only Memory (EPROM) or any other suitable technology. External memory 22 may include Random Access Memory (RAM) 233. RAM 233 may be a static RAM, battery backed up static RAM, Dynamic RAM (DRAM) or any other suitable technology. External memory 22 may include Electrically Erasable Programmable Read Only Memory (EEPROM) 235. External memory 22 may include Flash memory 234. External memory 22 may include a magnetic storage device such as disc 236. In some embodiments, external memory 22 may be included in a system, such as acoustic imaging system 100 shown in FIG. 1.

Figure 3:
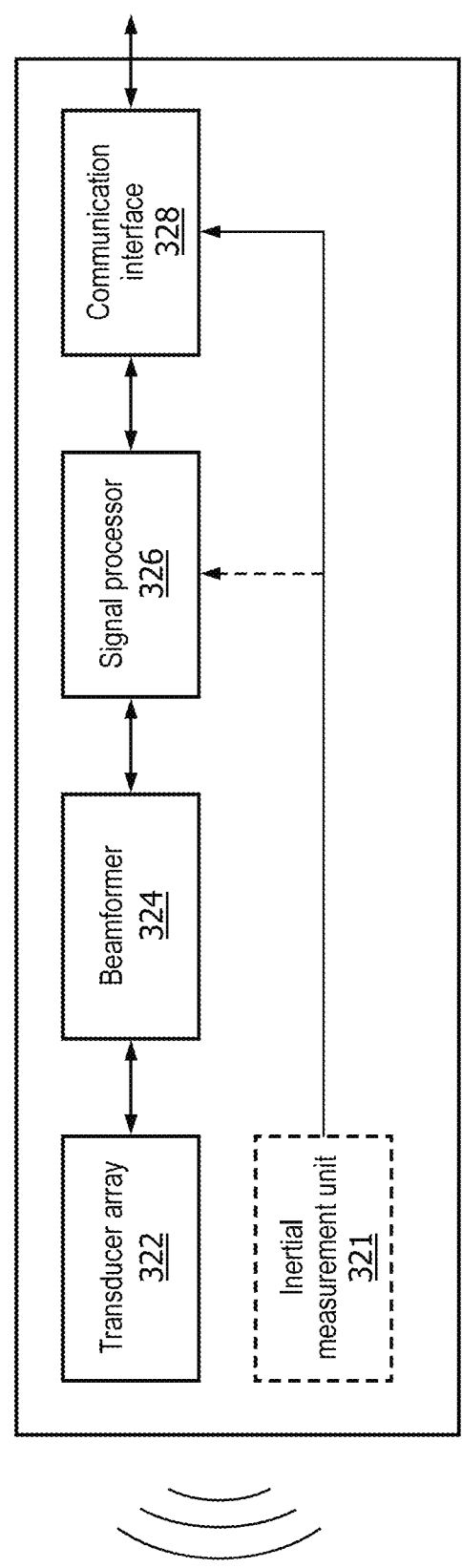
FIG. 3 illustrates an example embodiment of an acoustic probe.

FIG. 3 illustrates an example embodiment of acoustic probe 300. Acoustic probe 300 may include an array of acoustic transducer elements 322, a beamformer 324, a signal processor 326, and a communication interface 328. In various embodiments, acoustic transducer elements 322 may comprise, for example a two dimensional (2D) array or a linear or one dimensional (1D) array. For example, in some embodiments, transducer elements 322 may comprise piezoelectric elements. In operation, at least some of acoustic transducer elements 322 receive electrical transmit signals from transmit unit 113 of acoustic imaging instrument 110 and convert the electrical transmit signals to acoustic beams to cause the array of acoustic transducer elements 322 to transmit an acoustic probe signal 15 to an area of interest 10. Acoustic probe 300 may insonify an acoustic image plane in area of interest 10 and a relatively small region on either side of the acoustic image plane (i.e., it expands to a shallow field of view).

Also, at least some of acoustic transducer elements 322 of acoustic probe 300 receive acoustic echoes from area of interest 10 in response to acoustic probe signal 15 and convert the received acoustic echoes to one or more electrical signals representing an acoustic image of area of interest 10, in particular a two dimensional (2D) acoustic image. These electrical signals may be processed further by acoustic probe 300 and communicated by a communication interface 328 of acoustic probe 300 to receive unit 115 as one or more acoustic image signals.
300322322

In some embodiments, particularly in the case of an embodiment of acoustic probe 300 and acoustic imaging system 100 which is used in a training phase of a process or method as described in greater detail below for example with respect to FIG. 8, acoustic probe 300 may include or be associated with an inertial measurement unit 321, as described above, or another tracking device for obtaining relative orientation and position information for acoustic probe 300, and the 2D acoustic images obtained by acoustic imaging system 100 via acoustic probe 300 include or have associated therewith pose or tracking information for acoustic probe 300 while the 2D acoustic images are being acquired. In some embodiments, inertial measurement unit 321 may be a separate component not included within acoustic probe 300, but instead connected to or otherwise associated therewith, such as being affixed to or mounted on acoustic probe 300. Inertial measurement units per se are known to those of skill in the art. Inertial measurement unit 321 is configured to provide an inertial measurement signal to acoustic imaging instrument 110 which indicates a current orientation or pose of acoustic probe 300 so that a 3D volume and 3D acoustic image may be constructed from a plurality of 2D acoustic images obtained with different poses of acoustic probe 300.

In other embodiments, particularly in the case of an embodiment of acoustic probe 300 and acoustic imaging system 100 which is used in an application phase of a process or method as described in greater detail below for example with respect to FIG. 9, acoustic probe 300 does not include or utilize any inertial measurement unit 321, and the 2D acoustic images obtained by acoustic imaging system 100 via acoustic probe 300 do not include or have associated therewith any pose or tracking information for acoustic probe 300 while the 2D acoustic images are being acquired.

In some embodiments, one or more inertial measurement signals output by inertial measurement unit 421 may be supplied to communication interface 428 and thence to acoustic imaging instrument 110 where any desired processing may occur. In other embodiments, the one or more inertial measurement signals output by inertial measurement unit 321 may be supplied to signal processor 326 (instead of directly to communications interface 328) which may process the inertial measurement signal(s) as desired and provide processed inertial measurement signal(s) to communication interface 328, and thence to acoustic imaging instrument 110.

Disclosed in greater detail below are arrangements based on acoustic imaging systems such as acoustic imaging system 100 which may be employed in a method of fusing acoustic images, obtained in the absence of any tracking devices or systems, with images obtained via other imaging modalities, such as magnetic resonance imaging, MRI, computed tomography (CT), cone beam computed tomography (CBCT), etc.

In some embodiments, these arrangements include what is referred to herein as a "training framework" and what is referred to herein as an "application framework."

The training framework may execute a training process, as described in greater detail below, for example with respect to FIG. 8, using an embodiment of acoustic imaging system 100 which includes and utilizes IMU 321 and/or another tracking device or system which allows acoustic imaging system 100 to capture or acquire sets of spatially tracked two dimensional (2D) acoustic images.

The application framework may execute an application process, as described in greater detail below, for example with respect to FIG. 9, using an embodiment of acoustic imaging system 100 which does not include or utilize IMU 321 or another tracking device or system.

In some embodiments, the training framework may be established in a factory or laboratory setting, and training data obtained thereby may be stored on a data storage device, such as any of the external memories discussed above with respect to FIG. 2. Optimized parameters for a convolutional neural network of acoustic imaging system 100, as discussed in greater detail below, may also be stored on a data storage device, such as any of the external memories discussed above with respect to FIG. 2.

In some embodiments, the application framework may be defined in a clinical setting where an embodiment of acoustic imaging system 100 which does not include or utilize IMU 321 or another tracking device or system is used by a physician or clinician to obtain acoustic images of a subject or patient. In various embodiments, the data storage device which stores the optimized parameters for the convolutional neural network may be included in or connected, either directly or via a computer network, including in some embodiments the Internet, to an embodiment of acoustic imaging system 100 which executes the application framework. In some embodiments, optimized parameters for the convolutional neural network may be "hardwired" into the convolutional neural network of acoustic imaging system 100.

Summaries of embodiments of the training framework and the application framework will now be provided, followed by more detailed descriptions thereof.

In some embodiments, the following operations may be performed within the training framework.

(1) Acquisition of spatially tracked acoustic "sweeps" across a region of interest (i.e. sets of spatially tracked two dimensional (2D) acoustic images in a region of interest (ROI) or organ of interest in a subject population. In some embodiments, the number of images ($N_{image}$)≥20 and the number of subjects ($N_{subject}$)≥20.

(2) Acquisition of a 3D reference image of the same ROI or organ in the same or a similar subject population using another imaging modality, such as CT, MRI, CBCT, etc., which provides an absolute three dimensional reference frame for the 3D reference image.

(3) Reconstruction of a volumetric three dimensional (3D) acoustic image from each sweep of the tracked 2D acoustic images. This reconstruction also yields the pose of each constituent 2D acoustic image, $S_i$, within the 3D acoustic reconstruction coordinate system, i.e., the transformations $T_{2DUS\_to\_3DUS}$ for each 2D acoustic frame, i=1 .... $N_{image}$, which are computed based on the individual tracked poses of each 2D acoustic image $S_i$ in tracking coordinates, and the known pose of the 3D acoustic reconstruction in tracking coordinates.

(4) Segmenting the region of interest (ROI) or organ of interest in the three dimensional (3D) reference images.

(5) Defining a standardized 3D coordinate system based on the segmentations in the 3D reference images, e.g. defined by an origin of the coordinate system at the centroid of the segmentation, and rotation of the coordinate system to align the XY, XZ, and YZ planes with the axial, sagittal and coronal planes of the organ, or alternatively axial, sagittal, and coronal planes defined by the 3D reference imaging modality (i.e. patient orientation).

Although in the example above, it should be understood that the standardized 3D coordinate system could also have an origin at a vessel bifurcation and an axis oriented along one or two vessels; it could also have an origin at a distinguishable anatomical landmark, such as bony structure, etc. Every feature that one can manually or automatically define in the 3D reference image and relate to the acoustic image can be employed to define the standardized 3D coordinate system.

Figure 4:
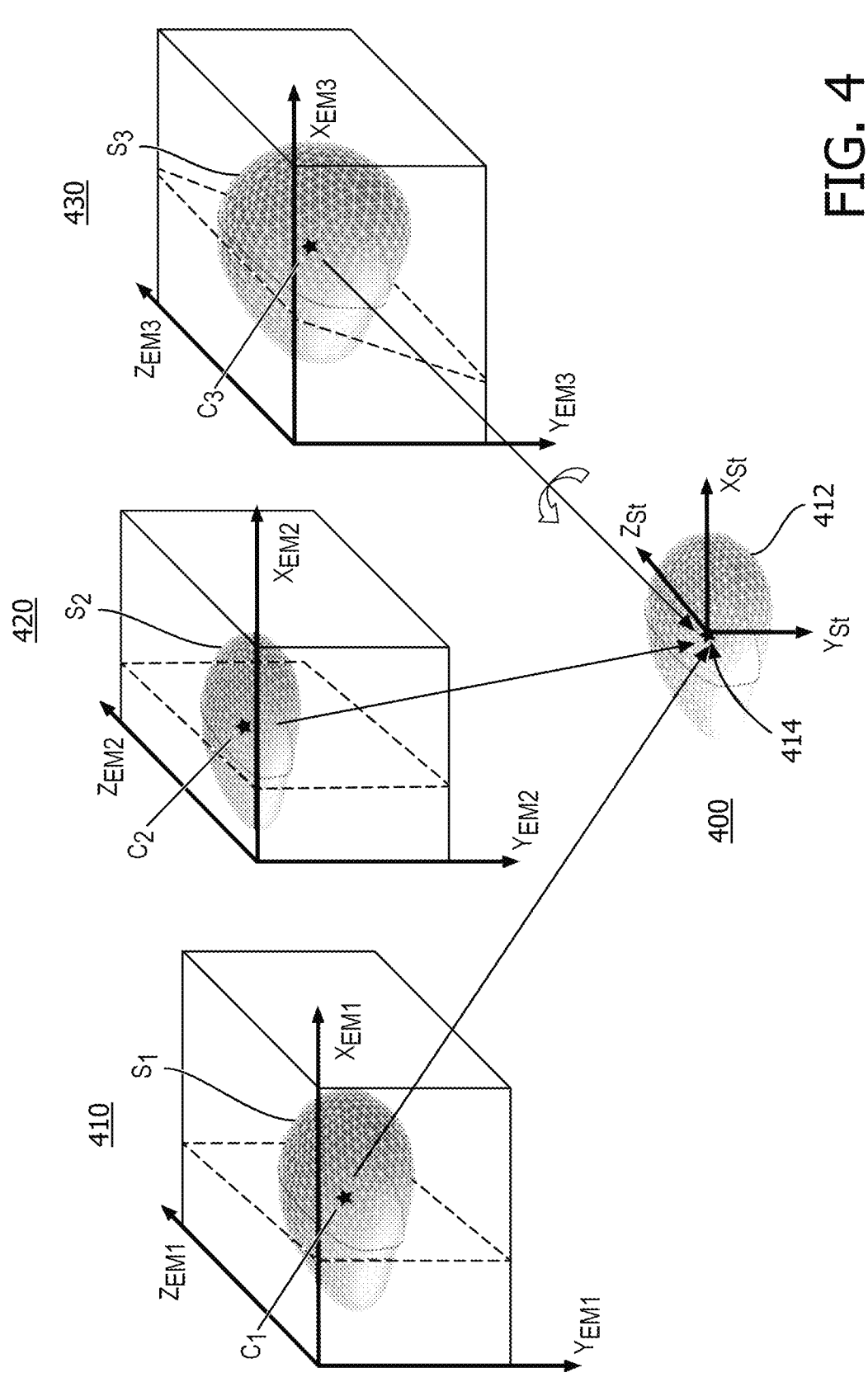
FIG. 4 illustrates an example of a definition of standardized organ-centered coordinate system.

FIG. 4 illustrates an example of a definition of standardized 3D coordinate system 400. Here, a 3D image of an organ 412 is obtained in several (e.g., three) patients, using an 3D imaging modality such as CT or MRI. Organ 412 is then segmented for each patient, providing the segmentations ($S_1$ to $S_n$, three shown) in the individual reference 3D coordinate systems ($EM_1$ to $EM_n$) for the 3D reference images. A standard anatomical plane, such as the midsagittal plane through the organ segmentation, is identified (described by the dashed line). Note that the center of the segmentation ($C_n$) and the orientation of the standard plane may differ from one acquisition to another. Likewise the angle of the mid-sagittal plane may differ in each 3D coordinate system.

For each acquisition, an organ-centered reference 3D coordinate system 410, 420, 430 is defined with origin 414 at the center of the segmentation, and the anatomical plane aligned with 2 of the coordinate axes of the standardized 3D coordinate system 400 (here: $Y_{St}$ and $Z_{St}$). The standard anatomical plane for each acquisition is not necessarily aligned with its organ-centered reference 3D coordinate system 410, 420, 430, although it may be.

(6) Registration of the 3D acoustic reconstruction with the 3D reference image, i.e., determining the transformation from acoustic 3D coordinates to reference 3D coordinates ($T_{3DUS\_to\_MRI}$), using methods known in the art.

(7) Training a convolutional neural network (CNN) to predict the 2D acoustic frame positions in the standardized 3D coordinates, by providing to the network input/output pairs (each 2D acoustic image $S_i$ paired with its actual standardized pose $T_i$ in standardized 3D coordinates) and performing an optimization of the parameters/weights of the CNN until the standardized predicted poses output by the CNN are optimally predicted compared to the actual standardized poses based on the 2D acoustic image input.

Figure 5:
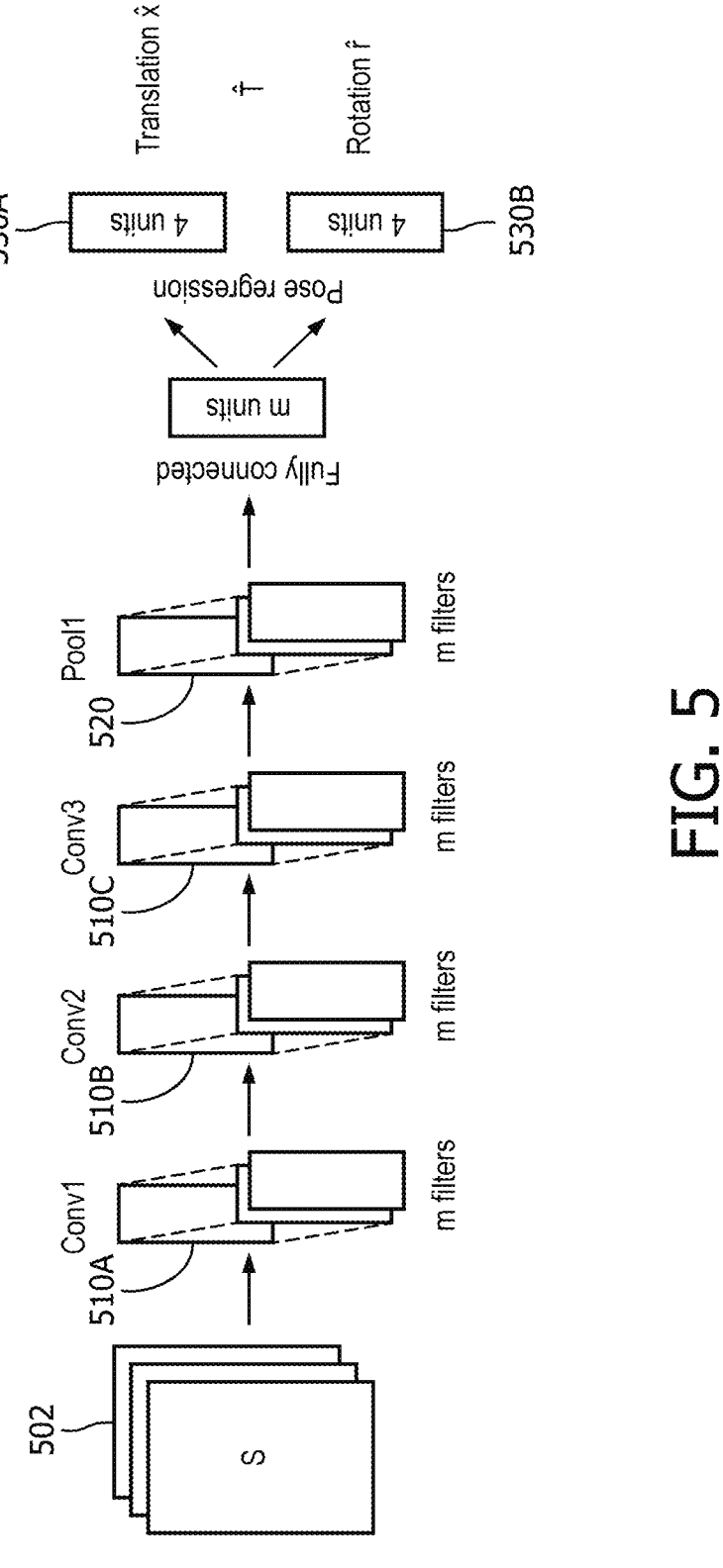
FIG. 5 depicts graphically an example of a deep convolutional neural network (CNN).

FIG. 5 depicts graphically an example of a deep convolutional neural network 500 which may be employed in the training phase and/or application phase of operation as described herein, and in greater detail with respect to FIGS. 8 and 9 below, for an acoustic imaging system such as acoustic imaging system 100. Convolutional neural network 500 processes input data sets 502. Convolutional neural network 600 includes a plurality of intermediate layers 510A, 510B, 510C and 510D. Convolutional neural network 500 may have more than four intermediate layers or fewer. Convolutional neural network 500 may have one or more final fully connected or global average pooling layer 520, followed by a plurality of regression layers 530A and 530B for regression of translational and rotational components of a rigid coordinate system transformation. Convolutional neural network 500 may have one regression layer, two layers or more than two layers. In one exemplary embodiment, the intermediate layers are convolutional layers, including convolution operations, non-linear regularization, batch normalization, and spatial pooling. This rigid transformation might have a vectorial or non-vectorial parametric representation and therefore the number and dimensions of last regression layers may vary. For instance, rotation can be represented as Euler angles, quaternions, matrix, exponential map, and angle-axis, whereas translation can be separated into direction and magnitude.

Convolutional neural network 500 may be trained using a batch-wise approach on the task to regress the rigid transformation given an input 2D ultrasound image.

During training, an input to convolutional neural network 500 is a 2D ultrasound image and the output is a standardized predicted pose of that 2D acoustic image with respect to a standardized 3D coordinate system. The input to the training framework is pairs of (2D acoustic image, actual poses). The optimizer in the training framework modifies the CNN's parameters so that the prediction for each image approximates the corresponding known actual pose in an optimal way (e.g. minimizing the sum of absolute differences of the pose parameters between prediction and actual pose) In operation after training, convolutional neural network 500 takes a currently produced 2D acoustic image of a subject and predicts the rigid transformation to yield a predicted pose for the 2D acoustic image in the standardized 3D coordinate system.

Accordingly, the training framework automatically generates a training dataset of 2D acoustic images of a region or organ of interest, and corresponding actual poses of those 2D acoustic images in the standardized 3D coordinate system using registration transformations between 3D acoustic coordinates and reference 3D coordinates for the 3D reference image provided by image registration methods that are known in the art, such as mutual-information based registration, or landmark-based registration. The training framework then uses the training dataset to train a neural network (e.g., convolutional neural network 500) using the training dataset to optimize the neural network's ability to predict poses for other 2D acoustic images of the region or organ of interest which are obtained without any tracking information.

In some embodiments, the following operations may be performed within the application framework.

(A) Acquisition of a 3D reference image in a subject, using a 3D imaging modality which allows segmentation of the ROI or reference structure (e.g., organ) within the ROI. This may be the same imaging modality as was used to acquire the 3D reference images during training, or another 3D imaging modality (e.g., MRI or CT) which allows segmentation of the ROI or reference structure (e.g., organ) within the ROI.

(B) Segmentation of an ROI or a reference structure (e.g., an organ) in an ROI in the 3D reference image.

(C) Defining a standardized 3D coordinate system in the same way as was done during the training phase as described above with respect to FIG. 4.

(D) Acquisition of at least one 2D acoustic image in the same subject without spatial tracking of the acoustic probe, in or near the same ROI or organ, i.e., within the area covered by at least one of the acoustic sweeps which were made during training.

(E) For each acquired 2D acoustic image, using the trained convolutional neural network, obtained during the training phase, to generate a standardized predicted pose for the 2D acoustic frame in the standardized 3D coordinate system.

(F) Converting the standardized 3D coordinates of each 2D acoustic image to the reference 3D coordinate system specific to the 3D reference image acquired for this subject. This converts each standardized predicted pose, in the standardized 3D coordinate system, to a reference predicted pose in the reference 3D coordinate system.

(G) Using the resulting reference predicted pose of the 2D acoustic image in reference 3D coordinates to co-display the 2D acoustic image(s) and the corresponding multi-planar reconstruction (MPR) from the 3D reference image, or otherwise visualize the spatial pose of the 2D acoustic image relative to the reference image in a clinically beneficial way.

Figure 6:
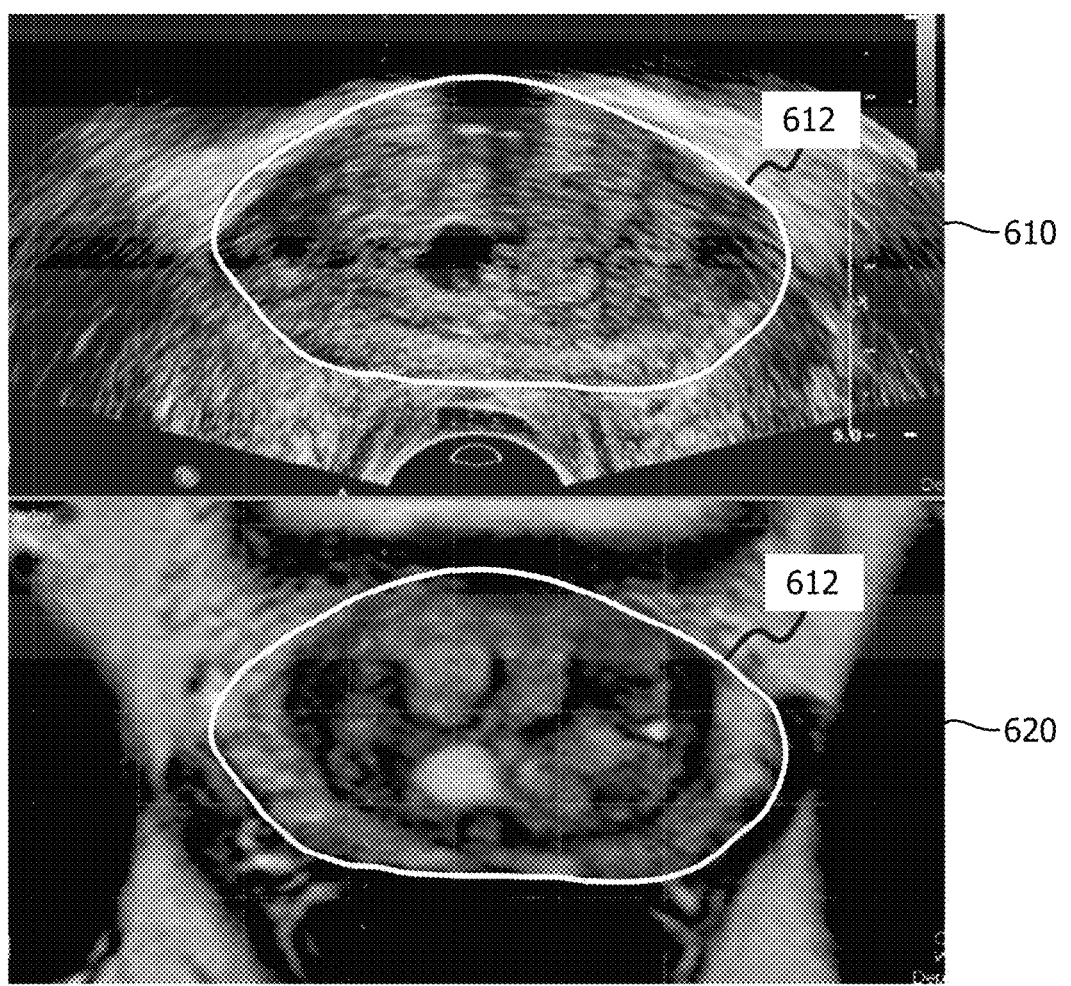
FIG. 6 illustrates a display of an example freehand two-dimensional (2D) acoustic image obtained for an organ, and corresponding multi-planar reconstruction (MPR) from an MRI scan in the same patient, based on a reference predicted pose of the acoustic image relative to the MRI in the three dimensional coordinate system of the MRI.

As an example, FIG. 6 illustrates a display of an example freehand two-dimensional acoustic image 610 obtained for an organ, and a corresponding multi-planar reconstruction (MPR) 620 from an magnetic resonance imaging (MRI) scan in the same subject, based on the predicted pose of the 3D acoustic image relative to the MRI image using the training framework and application framework described above. Here, as is well known in the art, freehand imaging refers to acoustic imaging where the operator moves the probe freely without respect to any particular orientation while capturing acoustic images of an area of interest. The contour 612 shows the intersection of the current view plane with the 3D segmentation of the organ of interest that was obtained from the MRI scan.

Various components of systems implementing the training framework and the application framework will now be described in greater detail.

Some embodiments of the training framework utilize a training dataset, a dataset processing controller (DPC), and a neural network training controller. In some embodiments, the DPC and/or the neural network training controller may comprise a processing system such as processing system 20 described above.

The training dataset consists of a collection of spatially tracked 2D acoustic image sweeps over a specific part of the anatomy (e.g., an organ) in a subject population (for example, a population of at least 20 subjects). In some embodiments, the subject population exhibits variations in age, size of the anatomy, pathology, etc. 3D acoustic volumes are reconstructed from 2D acoustic images using methods which are known in the art (e.g., Qing-Hua Huang, et al., "*Volume reconstruction of freehand three-dimensional ultrasound using median filters,*" ULTRASONICS 48, pp. 182-192, 2008). The acoustic probe (e.g., acoustic probe 300) which is used with an acoustic imaging system (e.g., acoustic imaging system 100) to obtain the spatially tracked 2D acoustic image sweeps can be tracked using one of the position measurement systems known in the art, such as optical tracking devices or systems, electromagnetic (EM) tracking devices or systems, IMU-based tracking, etc., Based on the spatial tracking of the acoustic probe while acquiring the 2D acoustic images, the transformation describing the pose of each 2D acoustic image $S_i$ relative to the reconstructed 3D acoustic volume, $T_{2DUS\_to\_3DUS}$, is known.

In addition to the spatially tracked and reconstructed acoustic imaging sweeps, a 3D reference image obtained via a different imaging modality, such as CT, MRI, CBCT, is also acquired in the same subject, and referred to herein as the 3D reference image. Each 3D acoustic volume is spatially registered to its corresponding 3D reference image by methods known in the art, e.g. manually, or semi-automatically as, e.g., implemented on the PHILIPS® URONAV® Fusion Biopsy System, yielding the registration transformation $T_{3DUS\_to\_MRI}$.

The dataset processing controller (DPC) is configured to: load a single case from the training dataset, segment the area of interest or organ of interest from the 3D reference images (e.g., CT, MRI, etc.); based on the segmented mask create a mesh using, e.g., a marching cubes algorithm that is known in the art; and based on the mesh define a standardized 3D coordinate system (see FIG. 4, discussed above) by setting the origin of the standardized 3D coordinate system at the centroid of the segmentation (the centroid is an arithmetic mean of all vertices ($p \epsilon R^3$) of the mesh), and setting the orientation of the 3D coordinate axes defined by the axial, coronal and sagittal planes of the organ or region of interest (e.g., identified via principal component analysis of the mesh).

The pose of the standardized 3D coordinate system relative to the reference 3D coordinate system for each reference image is expressed by the transformation $T_{MRI\_to\_MRIreference}$ (which in some cases may be the identity transform).

Optionally the DPC may preprocess one or more 2D acoustic images, for example by cropping the 2D acoustic image to a relevant rectangular region of interest.

The DPC may also compute the actual pose $T_i$ of each (potentially pre-processed) 2D acoustic image relative to the standardized 3D coordinate system using the equation:

$$T_i = T_{2DUS\_to\_MRIreference} = T_{MRI\_to\_MRIreference} * T_{3DUS\_to\_MRI} * T_{2DUS\_to\_3DUS}$$

where the "*" symbol indicates the matrix multiplication concatenating the pose transforms (from right to left).

At the end of these operations, a large set of 2-tuples $d_i$ may be provided:

$$d_i = (S_i, T_i),$$

where $S_i$ is an input ultrasound image and $T_i$ is a rigid transformation describing the position and orientation (herein referred to as the "actual pose") of the ultrasound image $S_i$ in the standardized 3D coordinate system. The DPC provides this set of 2-tuples $d_i$ to the network training controller.

The network training controller is configured to: receive the set of 2-tuples from the DPC, and batch-wise train the CNN using sets of the provided 2-tuples—that is to optimize parameters/weights of the CNN to minimize differences between the standardized predicted poses of the 2D acoustic images, which are output by the CNN, and the actual poses for all of the spatially tracked 2D acoustic images for all of the subjects, which are obtained as described above.

Thus, the output of the training framework may be an optimized set of parameters/weights for the CNN which maximizes the accuracy with which the CNN predicts unknown poses of 2D acoustic images which are input to it.

Some embodiments of the application framework utilize: an acoustic imaging system (e.g., acoustic imaging system 100); a pose prediction controller (PPC); and a multi-modality imaging controller. In some embodiments, the PPC and/or the multi-modality imaging controller may comprise a processing system such as processing system 20 described above. In some embodiments, the acoustic imaging system may include the PPC and/or the multi-modality imaging controller as part of a processing system (e.g., processing system 112) of the acoustic imaging system.

The acoustic imaging system preferably acquires 2D acoustic images of a region of interest, which may include an organ of interest, in the human body. The acoustic imaging system employs an acoustic probe, which in some embodiments may be a hand-held transrectal ultrasound (TRUS) or transthoracic echocardiography (TTE) transducer. In some cases where the organ of interest is large and there is a need to create a larger compound volumetric image, a 3D acoustic probe may be used. Whatever acoustic probe is employed, it does not include or utilize and is not associated with any tracking device, such as an IMU, EM tracker, optical tracker, etc. In other words, the acoustic imaging system does not acquire any tracking, location, orientation, or pose information for the acoustic probe as the acoustic probe is used to gather acoustic image data for the 2D acoustic images The PPC includes a deep neural network, for example a convolutional neural network (CNN) consisting of single or plurality of intermediate layers and last regression layers, for example as illustrated in FIG. 5. The number of intermediate convolutional layers may depend on the complexity of the region or organ of interest. Each convolutional layer may consist of a convolution, non-linear regularization, batch normalization and spatial pooling. The neural network may be trained using the aforementioned training dataset-processed by the TDC-on the task to predict a rigid transformation in in the standardized 3D coordinate system for a given current 2D acoustic image for which no position, orientation, pose or tracking information is available. Rigid transformation can be separated into translational and rotational components as specified by the last layer.

The PPC is configured to provide the CNN with an input 2D acoustic image, and to obtain from the CNN as an output the predicted standardized pose of the 2D acoustic image in the standardized coordinate system.

Optionally, in some embodiments pose predictions may be averaged over multiple 2D acoustic images, for example sequentially acquired 2D acoustic image, to improve robustness.

Optionally, in some embodiments the poses of the 2D acoustic images can be visualized in their respective locations in the standardized 3D coordinate system.

Figure 7:
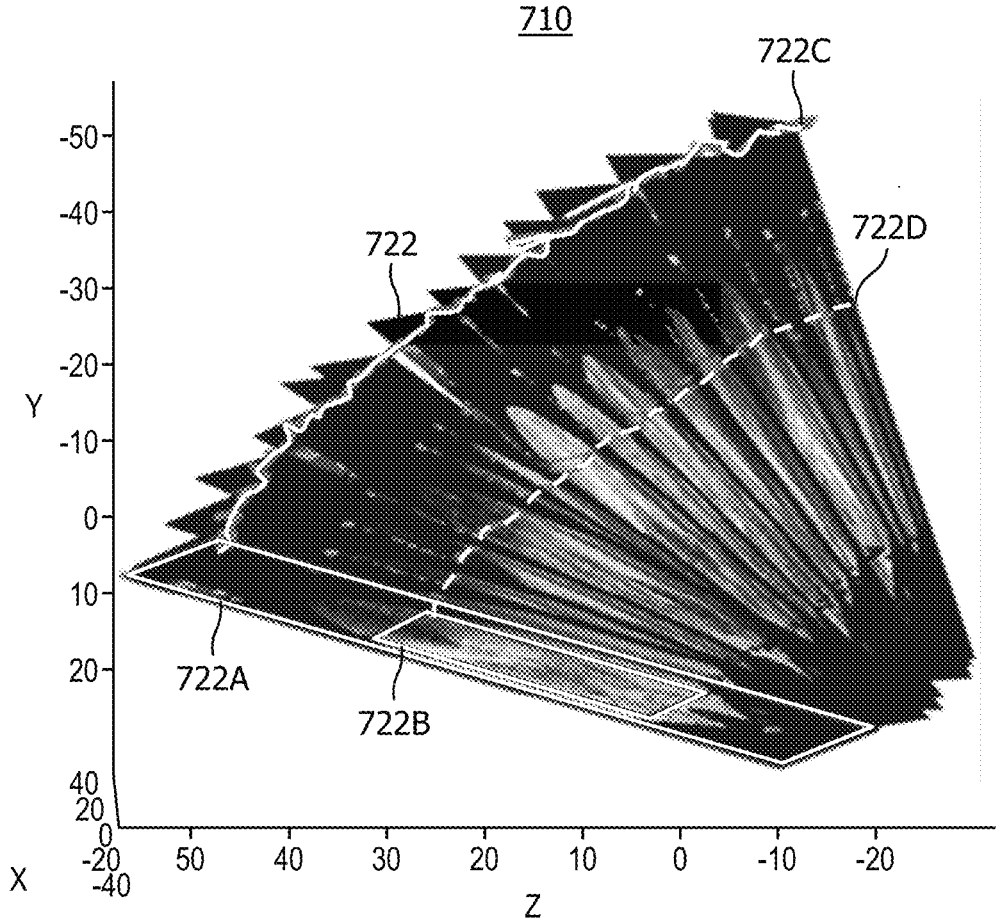
FIG. 7 depicts an example of localization of a sequence of un-tracked 2D acoustic images based on the predictions of a trained convolutional neural network.

FIG. 7 depicts an image 710 which shows an example of localization of a sequence of un-tracked 2D acoustic images 722 based on the predictions of a trained convolutional neural network (CNN). The pose predictions, here referred to as standardized predicted poses, are in a standardized 3D coordinate system, which is based on a segmentation of a region or organ of interest in an MRI scan of the same region or organ of interest. Here, the acoustic imaging user performed an angled sweep across the region or organ of interest during the acquisition, covering a cone-shaped region of interest, which is visible in the CNN-predicted, angled poses of the individual 2D acoustic images. The solid line 722A highlights the first frame in the sequence, and the solid line 722B highlights the rectangular ROI within the image frame that was used for the pose prediction. The "squiggly" line 722C shows the predicted trajectory of the upper left corner of the 2D acoustic image, and the dashed line 722D shows the predicted trajectory of the upper left corner of the ROI throughout the image acquisition sequence.

The multi-modality imaging controller uses a reference 3D image obtained in the same subject as the 2D ultrasound image, and the pose predicted by the pose prediction controller for an ultrasound image, to co-display the 2D acoustic image with a corresponding 2D plane from the reference 3D image, using methods known in the art, such as co-displaying the 2D acoustic image with a multi-planar reconstruction from the reference 3D image (see FIG. 6, discussed above).

Alternatively the pose predictions for a sequence of 2D acoustic image may be used to construct a 3D acoustic image of a volume in the region of interest, which can be used, e.g., to: perform volumetric measurements; create extended 3D acoustic imaging fields of view to show entire organs that are too large to be captured in a single 2D or 3D acoustic image; register the 3D acoustic image with 3D images from other imaging modalities for improved diagnosis or therapy guidance.

Figure 8:
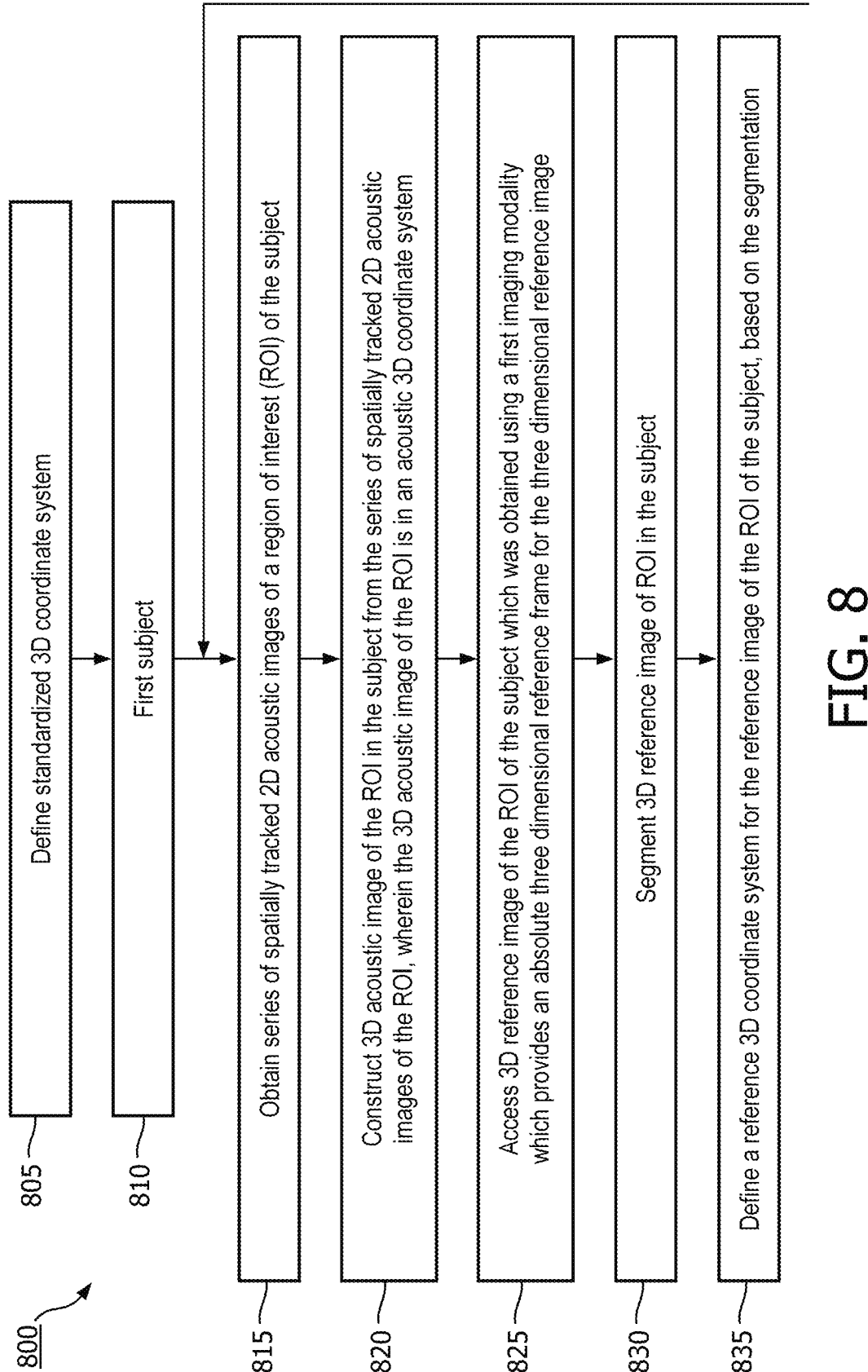
FIG. 8 illustrates a flowchart of an example embodiment of a method of training a convolutional neural network to provide accurate estimates of the pose of two dimensional acoustic images in a standardized three dimensional coordinate system.

FIG. 8 illustrates a flowchart 800 of an example embodiment of a method of training a convolutional neural network to provide accurate estimates of the pose of two dimensional acoustic images in a standardized three dimensional reference coordinate system.

An operation 805 includes defining a standardized three dimensional coordinate system for a plurality of three dimensional reference images of corresponding ROIs in a plurality of subjects, where the three dimensional reference images were obtained using a first imaging modality which provides an absolute three dimensional reference frame for the three dimensional reference image. The ROI may include a reference structure having a known shape and orientation in the body, for example an organ, a bone, a joint, one or more blood vessels, etc. In some embodiments, the standardized three dimensional coordinate system for the ROI may be defined by selecting an origin and three mutually orthogonal axes for the standardized three dimensional coordinate system based on a priori knowledge about an abstract reference structure (e.g., an abstract organ, such as a liver) in the ROI. Operation 810 may be performed using methods described above with respect to FIG. 4. For example, as explained above with FIG. 4, in some embodiments the standardized three dimensional coordinate system may be selected using the axial, sagittal, and coronal planes for an abstract reference structure, such as an organ An operation 810 includes selecting a first subject for the subsequent operations 815 through 845. In the subsequent operations 815 through 845 the subject will be the first subject on the first iteration through the loop (steps 815 through 845) and a different subject for each of the next iterations through the loop. Here the first subject may be selected in any convenient way, for example randomly, as the order in which subjects are selected is irrelevant to the method of FIG. 8.

An operation 815 includes obtaining a series of spatially tracked two dimensional acoustic images of the ROI in the subject.

An operation 820 includes constructing a three dimensional acoustic image of the ROI in the subject from the series of spatially tracked two dimensional acoustic images of the ROI obtained in operation 815, where the three dimensional acoustic image of the ROI in the subject is in an acoustic three dimensional coordinate system.

An operation 825 includes accessing a selected three dimensional reference image among the plurality three dimensional reference images, where the selected three dimensional reference image is of the ROI in the subject.

An operation 830 includes segmenting the three dimensional reference image of the ROI in the subject.

An operation 835 includes defining a reference three dimensional coordinate system for the reference image of the ROI in the subject, based on the segmentation.

An operation 840 includes determining for each of the spatially tracked two dimensional acoustic images of the ROI in the subject its actual pose in the standardized three dimensional coordinate system. The actual pose is determined from a pose of the spatially tracked two dimensional acoustic image in the acoustic three dimensional coordinate system, a first coordinate transformation from the acoustic three dimensional coordinate system to the reference three dimensional coordinate system, and a second coordinate transformation from the reference three dimensional coordinate system to the standardized three dimensional coordinate system.

An operation 845 includes determining whether the subject is the last subject that should pass through the loop. If the subject is not the last subject, then the process returns to operation 815, and operations 815 through 845 are performed for a next subject. Here the next subject may be selected in any convenient way, for example randomly, as the order in which subjects are selected is irrelevant to the method of FIG. 8, as explained above. If the subject is the last subject, then the process proceeds to operation 850.

An operation 850 includes performing an optimization process on a convolutional neural network (CNN) by providing the spatially tracked 2D acoustic images to the CNN and adjusting parameters of the CNN to minimize differences between predicted poses generated by the CNN for the spatially tracked 2D acoustic images and the actual poses of the spatially tracked 2D acoustic images. In some embodiments, operation 850 may be performed "batch-wise", i.e. by sequentially taking random subsets (e.g. 16, or 32) of the groups of images across a plurality of subjects and feeding them as inputs to the CNN for the next optimization step During the training process, weights of the CNN may be constantly updated by propagating errors between predicted and actual pose values for the poses given an input image that is fed to the CNN.

Figure 9:
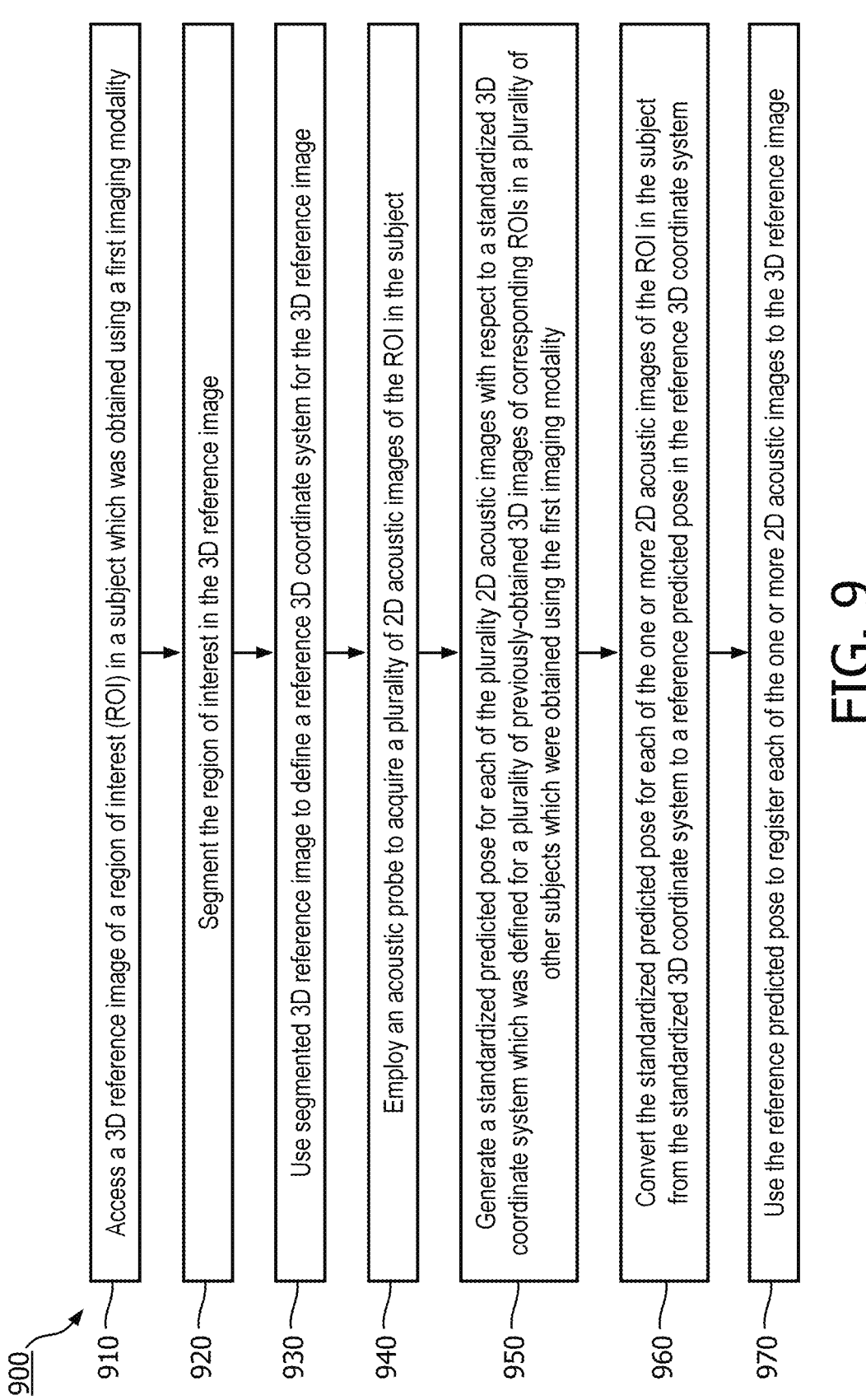
FIG. 9 illustrates a flowchart of an example embodiment of a method of fusing acoustic images obtained in the absence of any tracking devices with images obtained via other imaging modalities, such as MRI.

FIG. 9 illustrates a flowchart 900 of an example embodiment of a method of fusing acoustic images obtained in the absence of any tracking devices with images obtained via other imaging modalities, such as MRI.

As an input to the method of FIG. 9, a three dimensional reference image of a region of interest (ROI) in a subject was obtained using a first imaging modality which provides an absolute three dimensional reference frame for the three dimensional reference image. An operation 910 includes accessing this three dimensional reference image An operation 920 includes segmenting the ROI in the three dimensional reference image.

An operation 930 includes employing the segmented ROI in the three dimensional reference image to define a reference three dimensional coordinate system for the three dimensional reference image. The reference three dimensional coordinate system may be defined as described above with respect to FIG. 4.

An operation 940 includes employing an acoustic probe to acquire two dimensional acoustic images of the ROI in the subject without spatial tracking of the acoustic probe.

An operation 950 includes predicting a pose for each of one or more of the two dimensional acoustic images of the ROI in the subject with respect to a standardized three dimensional coordinate system which was defined, for example as described above with respect to FIG. 4, for a plurality of previously-obtained three dimensional images of corresponding ROIs in a plurality of other subjects which were obtained using the first imaging modality.

An operation 960 includes converting the standardized predicted pose for each of the one or more two dimensional acoustic images of the ROI in the subject from the standardized three dimensional coordinate system to a reference predicted pose in the reference three dimensional coordinate system.

An operation 970 includes using the reference predicted pose to register each of the one or more two dimensional acoustic images to the three dimensional reference image.

While preferred embodiments are disclosed in detail herein, many variations are possible which remain within the concept and scope of the invention. Such variations would become clear to one of ordinary skill in the art after inspection of the specification, drawings and claims herein. The invention therefore is not to be restricted except within the scope of the appended claims.

What is claimed is:

1. A system for registering two dimensional acoustic images to a three dimensional reference image, and configured to communicate with an acoustic probe, wherein the acoustic probe has an array of acoustic transducer elements, wherein the acoustic probe is not associated with any tracking device, wherein the acoustic probe is configured to transmit one or more acoustic signals to a region of interest (ROI) in a subject, and wherein the acoustic probe is configured to receive acoustic echoes from the region of interest, comprising:

an acoustic imaging instrument configured to connect to the acoustic probe, the acoustic imaging instrument comprising a communication interface and a processing system, wherein the communication interface is configured to provide transmit signals to at least some of the acoustic transducer elements, wherein the transmit signals cause the array of acoustic transducer elements to transmit the one or more acoustic signals to the ROI in the subject, wherein the communication interface is configured to receive one or more image signals from the acoustic probe, wherein the image signals are produced from the acoustic echoes, wherein the processing system is configured to access a three dimensional reference image of the ROI in the subject, wherein the three dimensional reference image is obtained using a first imaging modality, wherein the processing system is configured to segment the ROI in the three dimensional reference image, wherein the processing system is configured to employ the segmented ROI in the three dimensional reference image to define a reference three dimensional coordinate system for the three dimensional reference image, wherein the processing system is configured to acquire a plurality of two dimensional acoustic images of the ROI in the subject from the image signals, wherein the processing system is configured to generate a standardized predicted pose using a trained convolutional neural network (CNN), for each of the plurality two dimensional acoustic images of the ROI with respect to a standardized three dimensional coordinate system, wherein the standardized three dimensional coordinate system was defined for a plurality of previously-obtained three dimensional images of corresponding ROIs in a plurality of other subjects, wherein the plurality of previously-obtained three dimensional images of corresponding ROIs were obtained using the first imaging modality, wherein the processing system is configured to convert the standardized predicted pose for each of the two dimensional acoustic images of the ROI in the subject from the standardized three dimensional coordinate system to a reference predicted pose in the reference three dimensional coordinate system; and wherein the processing system is configured to use the reference predicted pose to register each of the two dimensional acoustic images to the three dimensional reference image, and further wherein the CNN is trained by:

defining a standardized three dimensional coordinate system for a plurality of three dimensional reference images of corresponding ROIs in a plurality of subjects, wherein the three dimensional reference images were obtained using a first imaging modality;

for each of the plurality of subjects:

obtaining a series of spatially tracked two dimensional acoustic images of the ROI in the subject;

constructing a three dimensional acoustic image of the ROI in the subject from the series of spatially tracked two dimensional acoustic images of the ROI, wherein the three dimensional acoustic image of the ROI in the subject is in an acoustic three dimensional coordinate system;

accessing a selected three dimensional reference image among the plurality three dimensional reference images, wherein the selected three dimensional reference image is of the ROI in the subject;

segmenting the three dimensional reference image of the ROI in the subject;

defining a reference three dimensional coordinate system for the reference image of the ROI in the subject, based on the segmentation; and determining for each of the spatially tracked two dimensional acoustic images of the ROI in the subject its actual pose in the standardized three dimensional coordinate system using: a pose of the spatially tracked two dimensional acoustic image in the acoustic three dimensional coordinate system, a first coordinate transformation from the acoustic three dimensional coordinate system to the reference three dimensional coordinate system, and a second coordinate transformation from the reference three dimensional coordinate system to the standardized three dimensional coordinate system; and performing an optimization process on the CNN by providing the spatially tracked two dimensional acoustic images, and the corresponding actual poses of the spatially tracked two dimensional acoustic images, to the CNN and adjusting parameters of the CNN to minimize differences between predicted poses generated by the CNN for the spatially tracked two dimensional acoustic images and the actual poses of the spatially tracked 2D acoustic images.

2. The system of claim 1, further comprising a display device, wherein the system is configured to display on the display device at least one of the two dimensional acoustic images together with a corresponding two dimensional slice of the three dimensional reference image.

3. The system of claim 1, further comprising a display device, wherein the system is configured to use the standardized predicted poses to display on the display device a plurality of two dimensional acoustic images in the standardized three dimensional coordinate system.

4. The system of claim 1, wherein the processing system is further configured to construct a three dimensional acoustic image for the ROI in the subject from the two dimensional acoustic images and their corresponding reference predicted poses.

5. The system of claim 4, further comprising a display device, wherein the system is configured to display on the display device the reference three dimensional image and the three dimensional acoustic image in a common three dimensional coordinate system.

6. The system of claim 1, wherein the ROI in the subject includes an organ, and wherein segmenting the ROI in the three dimensional reference image comprises segmenting the organ.

7. The system of claim 1, wherein generating the standardized predicted pose for each of the two dimensional acoustic images of the ROI in the subject with respect to the standardized three dimensional coordinate system comprises applying each of the two dimensional acoustic images to the CNN.

8. The system of claim 1, wherein the two dimensional acoustic images comprise a series of two dimensional images, wherein generating the standardized predicted pose for each of the two dimensional acoustic images of the ROI in the subject with respect to the standardized three dimensional coordinate system comprises generating standardized predicted poses for the series of two dimensional images by averaging the standardized predicted poses over all of the two dimensional acoustic images of the series.

9. A method, comprising:

accessing a three dimensional reference image of a region of interest (ROI) in a subject, wherein the three dimensional reference image is obtained using a first imaging modality;

segmenting the ROI in the three dimensional reference image;

employing the segmented ROI in the three dimensional reference image to define a reference three dimensional coordinate system for the three dimensional reference image;

employing an acoustic probe to acquire a plurality of two dimensional acoustic images of the ROI in the subject without spatial tracking of the acoustic probe;

generating a standardized predicted pose, using a trained convolutional neural network (CNN), for each of the plurality of two dimensional acoustic images of the ROI in the subject with respect to a standardized three dimensional coordinate system, wherein the standardized three dimensional coordinate system was defined for a plurality of previously-obtained three dimensional images of corresponding ROIs in a plurality of other subjects, wherein the plurality of previously-obtained three dimensional images of corresponding ROIs were obtained using the first imaging modality;

converting the standardized predicted pose for each of the plurality of two dimensional acoustic images of the ROI in the subject from the standardized three dimensional coordinate system to a reference predicted pose in the reference three dimensional coordinate system; and using the reference predicted pose to register each of the two dimensional acoustic images to the three dimensional reference image, and further wherein the CNN is trained by:

defining a standardized three dimensional coordinate system for a plurality of three dimensional reference images of corresponding ROIs in a plurality of subjects, wherein the three dimensional reference images were obtained using a first imaging modality;

for each of the plurality of subjects:

obtaining a series of spatially tracked two dimensional acoustic images of the ROI in the subject;

constructing a three dimensional acoustic image of the ROI in the subject from the series of spatially tracked two dimensional acoustic images of the ROI, wherein the three dimensional acoustic image of the ROI in the subject is in an acoustic three dimensional coordinate system;

accessing a selected three dimensional reference image among the plurality three dimensional reference images, wherein the selected three dimensional reference image is of the ROI in the subject;

segmenting the three dimensional reference image of the ROI in the subject;

defining a reference three dimensional coordinate system for the reference image of the ROI in the subject, based on the segmentation; and determining for each of the spatially tracked two dimensional acoustic images of the ROI in the subject its actual pose in the standardized three dimensional coordinate system using: a pose of the spatially tracked two dimensional acoustic image in the acoustic three dimensional coordinate system, a first coordinate transformation from the acoustic three dimensional coordinate system to the reference three dimensional coordinate system, and a second coordinate transformation from the reference three dimensional coordinate system to the standardized three dimensional coordinate system; and performing an optimization process on the CNN by providing the spatially tracked two dimensional acoustic images, and the corresponding actual poses of the spatially tracked two dimensional acoustic images, to the CNN and adjusting parameters of the CNN to minimize differences between predicted poses generated by the CNN for the spatially tracked two dimensional acoustic images and the actual poses of the spatially tracked 2D acoustic images.

10. The method of claim 9, further comprising displaying on a display device at least one of the two dimensional acoustic images together with a corresponding two dimensional slice of the three dimensional reference image.

11. The method of claim 9, further comprising using the standardized predicted poses to display on a display device a plurality of two dimensional acoustic images in the standardized three dimensional coordinate system.

12. The method of claim 9, further comprising constructing a three dimensional acoustic image for the ROI in the subject from the two dimensional acoustic images and their corresponding predicted poses.

13. The method of claim 12, further comprising displaying on a display device the reference three dimensional image and the three dimensional acoustic image in a common three dimensional coordinate system.

14. The method of claim 9, wherein the ROI in the subject includes an organ, and wherein segmenting the ROI in the three dimensional reference image comprises segmenting the organ.

15. The method of claim 9, wherein generating the standardized predicted pose for each of the two dimensional acoustic images of the ROI in the subject with respect to the standardized three dimensional coordinate system comprises applying each of the two dimensional acoustic images to the CNN.

16. The method of claim 9, wherein the two dimensional acoustic images comprise a series of two dimensional images, wherein generating the standardized predicted pose for each of the two dimensional acoustic images of the ROI in the subject with respect to the standardized three dimensional coordinate system comprises generating standardized predicted poses for the series of two dimensional images by averaging the standardized predicted poses over all of the two dimensional acoustic images of the series.

* * * * *